US008795718B2

(12) United States Patent
Bedard et al.

(10) Patent No.: US 8,795,718 B2
(45) Date of Patent: Aug. 5, 2014

(54) FUNCTIONAL NANO-LAYERED HEMOSTATIC MATERIAL/DEVICE

(75) Inventors: Robert L. Bedard, McHenry, IL (US); Steven A. Wilcher, Glencoe, IL (US)

(73) Assignee: Honeywell International, Inc., Morristown, NJ (US)

( * ) Notice: Subject to any disclaimer, the term of this patent is extended or adjusted under 35 U.S.C. 154(b) by 156 days.

(21) Appl. No.: 12/125,096

(22) Filed: May 22, 2008

(65) Prior Publication Data

US 2009/0291124 A1 Nov. 26, 2009

(51) Int. Cl.
*A61L 15/18* (2006.01)
*A61L 15/42* (2006.01)
*A61L 15/44* (2006.01)

(52) U.S. Cl.
CPC ........... *A16L 15/18* (2013.01); *A61L 2300/606* (2013.01); *A61L 2400/04* (2013.01); *A61L 2300/418* (2013.01); *A61L 2300/45* (2013.01); *A61L 15/44* (2013.01); *A61L 2400/12* (2013.01); *A61L 2300/10* (2013.01)
USPC ........... 424/445; 424/447; 424/684; 424/688; 424/724; 424/601; 424/682; 442/59; 442/123

(58) Field of Classification Search
CPC ..... A61L 15/18; A61L 15/44; A61L 2300/10; A61L 2300/418; A61L 2300/45; A61L 2300/606; A61L 2400/04; A61L 2400/12
See application file for complete search history.

(56) References Cited

U.S. PATENT DOCUMENTS

| | | | |
|---|---|---|---|
| 3,628,534 A | 12/1971 | Donohue | |
| 3,993,640 A | 11/1976 | Pickard et al. | |
| 4,051,848 A * | 10/1977 | Levine | 604/304 |
| 4,104,226 A | 8/1978 | Melzer et al. | |
| 4,282,059 A | 8/1981 | Davidson | |
| 4,454,055 A | 6/1984 | Richman et al. | |
| 4,525,410 A | 6/1985 | Hagiwara et al. | 428/198 |
| 4,775,585 A | 10/1988 | Hagiwara et al. | 428/323 |
| 4,822,349 A | 4/1989 | Hursey et al. | 604/367 |
| 4,826,497 A | 5/1989 | Marcus et al. | 604/359 |
| 4,911,898 A | 3/1990 | Hagiwara et al. | 423/118 |
| 4,938,958 A | 7/1990 | Niira et al. | 424/79 |
| 4,959,268 A | 9/1990 | Hagiwara et al. | 428/403 |
| 5,064,599 A | 11/1991 | Ando et al. | 264/237 |
| 5,084,427 A | 1/1992 | Tsoucalas | 502/62 |
| 5,104,411 A * | 4/1992 | Makoui et al. | 8/116.4 |
| 5,120,693 A | 6/1992 | Connolly et al. | 502/64 |
| 5,470,585 A | 11/1995 | Gilchrist | 424/604 |
| 5,489,469 A | 2/1996 | Kobayashi et al. | 428/283 |
| 5,503,908 A | 4/1996 | Faass | 428/198 |
| 5,556,699 A | 9/1996 | Niira et al. | 428/323 |
| 5,614,570 A | 3/1997 | Hansen et al. | 524/13 |
| 5,643,589 A | 7/1997 | Chalmers | 424/404 |
| 5,650,221 A | 7/1997 | Belding et al. | |
| 5,744,404 A | 4/1998 | Titterton et al. | 442/63 |
| 5,800,372 A | 9/1998 | Bell et al. | 602/48 |
| 5,874,164 A | 2/1999 | Caldwell | |
| 5,981,052 A | 11/1999 | Sugiyama | 428/311.71 |
| 6,060,461 A | 5/2000 | Drake | 514/54 |
| 6,102,107 A | 8/2000 | Dunne | |
| 6,123,925 A | 9/2000 | Barry et al. | 424/49 |
| 6,187,347 B1 | 2/2001 | Patterson et al. | 424/646 |
| 6,229,062 B1 | 5/2001 | Mandell et al. | |
| 6,277,772 B1 | 8/2001 | Gancet et al. | 442/327 |
| 6,441,265 B1 | 8/2002 | Chan | 602/53 |
| 6,472,162 B1 | 10/2002 | Coelho et al. | 435/13 |
| 6,486,378 B1 * | 11/2002 | Areskoug et al. | 602/41 |
| 6,495,367 B1 | 12/2002 | Isogawa et al. | 436/18 |
| 6,521,265 B1 | 2/2003 | Patterson | 424/646 |
| 6,592,888 B1 | 7/2003 | Jensen et al. | 424/443 |
| 6,632,678 B2 | 10/2003 | Aiken et al. | 436/69 |
| 6,638,296 B2 | 10/2003 | Levinson | 606/213 |
| 6,700,032 B1 | 3/2004 | Gray | |
| 6,712,934 B2 | 3/2004 | Ahlgren et al. | |
| 6,790,429 B2 | 9/2004 | Ciampi | 423/594.1 |
| 6,890,342 B2 | 5/2005 | Zhu et al. | 606/213 |
| 6,890,344 B2 | 5/2005 | Levinson | 606/213 |
| 6,974,562 B2 | 12/2005 | Ciampi et al. | 422/199 |
| 6,991,802 B1 * | 1/2006 | Ahola et al. | 424/423 |
| 6,992,233 B2 | 1/2006 | Drake et al. | 602/48 |
| 6,998,510 B2 | 2/2006 | Buckman et al. | 602/48 |
| 7,019,191 B2 | 3/2006 | Looney et al. | |
| 7,056,722 B1 | 6/2006 | Coelho et al. | 435/214 |
| 7,074,981 B2 | 7/2006 | Chalmers | 602/41 |
| 7,252,837 B2 | 8/2007 | Guo et al. | |

(Continued)

FOREIGN PATENT DOCUMENTS

AU 2006203585 9/2006
EP 0 095 922 * 12/1983

(Continued)

OTHER PUBLICATIONS

Hyde et al., Journal of Biotechnology, 6: 213-223 (2011).*

(Continued)

*Primary Examiner* — Kortney L Klinkel
*Assistant Examiner* — Lisbeth C Robinson

(57) ABSTRACT

The present invention utilizes a nano-coating of an oxide such as silica, a silicate or another effective oxide on a surface to accelerate blood clotting in mammalian animals. The hemostatic layer has a thickness that is effective for the hemostasis, yet can be made thin enough to result in a resorbable film which can either be applied to a biocompatible or resorbable device that can be used in surgical applications as well as in topical applications such as trauma.

6 Claims, No Drawings

(56) References Cited

U.S. PATENT DOCUMENTS

| | | |
|---|---|---|
| 7,582,308 B2 * | 9/2009 | Quincy et al. ............... 424/402 |
| 2001/0009831 A1 | 7/2001 | Schink et al. ............... 442/123 |
| 2002/0015726 A1 | 2/2002 | Scamilla Aledo et al. |
| 2003/0133990 A1 | 7/2003 | Hursey et al. ............... 424/601 |
| 2003/0157346 A1 * | 8/2003 | Kawamura et al. ........... 428/451 |
| 2003/0208150 A1 | 11/2003 | Bruder et al. ................... 602/48 |
| 2003/0224056 A1 * | 12/2003 | Kotha et al. ................... 424/489 |
| 2004/0116018 A1 | 6/2004 | Fenwick et al. ............. 442/164 |
| 2004/0137812 A1 * | 7/2004 | Suzuki et al. ................. 442/59 |
| 2005/0058721 A1 | 3/2005 | Hursey ......................... 424/618 |
| 2005/0074505 A1 | 4/2005 | Hursey |
| 2005/0221707 A1 * | 10/2005 | Suzuki et al. ................. 442/230 |
| 2005/0226916 A1 | 10/2005 | Cochrum et al. ........... 424/445 |
| 2006/0034935 A1 | 2/2006 | Pronovost et al. |
| 2006/0039994 A1 | 2/2006 | Davis ........................... 424/601 |
| 2006/0078628 A1 | 4/2006 | Koman et al. ............... 424/672 |
| 2006/0127437 A1 | 6/2006 | Kennedy |
| 2006/0141060 A1 | 6/2006 | Hursey et al. ............... 424/684 |
| 2006/0155235 A1 | 7/2006 | Sawyer ........................... 602/48 |
| 2006/0178609 A1 | 8/2006 | Horn et al. ..................... 602/48 |
| 2006/0211965 A1 | 9/2006 | Horn et al. ..................... 602/13 |
| 2006/0211971 A1 | 9/2006 | Horn et al. ..................... 602/41 |
| 2007/0104768 A1 | 5/2007 | Huey et al. |
| 2007/0154509 A1 | 7/2007 | Wilcher et al. ............... 424/422 |
| 2007/0154510 A1 | 7/2007 | Wilcher et al. ............... 424/422 |
| 2007/0160653 A1 | 7/2007 | Fischer et al. |
| 2007/0275073 A1 | 11/2007 | Huey et al. |
| 2009/0137043 A1 * | 5/2009 | Parsons et al. ............... 435/398 |
| 2009/0148502 A1 | 6/2009 | Pronovost |
| 2009/0155342 A1 | 6/2009 | Diegelmann et al. |
| 2009/0232902 A1 | 9/2009 | Liu |
| 2010/0047352 A1 | 2/2010 | Pronovost et al. |

FOREIGN PATENT DOCUMENTS

| | | |
|---|---|---|
| EP | 0389015 A2 | 2/1990 |
| EP | 0888783 A1 | 6/1998 |
| EP | 1 738 779 A1 | 1/2007 |
| EP | 1 797 850 A1 | 6/2007 |
| EP | 1 810 697 A2 | 7/2007 |
| GB | 2259858 A | 8/1991 |
| JP | 57077623 | 5/1982 |
| JP | 60-195452 A | 10/1985 |
| JP | 61145120 | 7/1986 |
| JP | 62153215 | 7/1987 |
| JP | 3026254 | 2/1991 |
| JP | 1992-146218 | 5/1992 |
| JP | 4144565 | 5/1992 |
| JP | 7112021 | 5/1995 |
| JP | 8105885 | 4/1996 |
| JP | 8294527 | 12/1996 |
| JP | 2001-322926 A | 11/2001 |
| JP | 2007144154 | 6/2007 |
| JP | 2008531498 | 8/2008 |
| KR | 20040002799 | 1/2004 |
| WO | WO 93/01819 | 2/1993 |
| WO | WO 01/64148 A1 | 9/2001 |
| WO | WO 02/30479 * | 4/2002 |
| WO | WO 02/30479 A1 | 4/2002 |
| WO | WO 2005/027808 A1 | 3/2005 |
| WO | 2006012541 | 2/2006 |
| WO | WO 2006/071748 A2 | 7/2006 |
| WO | WO 2006/088912 A2 | 8/2006 |
| WO | WO 2007/081996 A2 | 7/2007 |
| WO | 2012007363 | 1/2012 |

OTHER PUBLICATIONS

Xiao et al. "Cationic-Modified Cyclodextrin Nanosphere/Anionic Polymer as Flocculation/Sorption Systems," Journal of Colloid and Interface Sciences; vol. 283, p. 406-413 (2005); Canada.

XP 002674712, Database WPI, Week 200220, Thomson Scientific, London, GB; AN 2002-151557, & JP 2001 322926 A, Nov. 20, 2001; Abstract.

XP002674713, Database WPI, Week 198546, Thomson Scientific, London, GB; AN 1985-286304, & JP 60 195452, Oct. 3, 1985; Abstract.

* cited by examiner

FUNCTIONAL NANO-LAYERED HEMOSTATIC MATERIAL/DEVICE

FIELD OF THE INVENTION

This invention relates generally to the use of nano-coatings of oxides to stop bleeding. More particularly, this invention relates to ultra-thin layers of oxides on the surfaces of materials to provide effective control of bleeding. These formulations contain a sufficient thickness of these oxides to stop blood loss and under certain conditions can dissolve when no longer needed to continue to function as a hemostatic device.

BACKGROUND OF THE INVENTION

Wounds are generally classified as acute or chronic in accordance with their healing tendencies. Acute wounds from trauma or surgery include wounds such as active bleeding wound sites, e.g., wounds that have detectable, unclotted blood. The rapid control of topical bleeding at active bleeding wound sites is of critical importance in wound management, especially for the management of trauma, e.g., as a result of military exercises or surgery.

Conventional approaches such as manual pressure, cauterization, or sutures may be time consuming and are not always effective in controlling bleeding. Trauma care has received great attention recently as United States troops on a daily basis face combat situations that result in wounds accompanied by significant blood loss. In many cases, the individual may have been able to survive the initial injury only to die of blood loss. Given the central role of hemostasis in trauma care, a great deal of attention has been focused on developing products that can rapidly induce clotting, stop the bleeding, form a tight bond to the wound surface, facilitate scab formation and be compatible with the host tissue. Currently there are several categories of products being used that can be differentiated by their mechanism of action. The first category includes materials that accelerate the coagulation process by absorbing water from the blood. The products in this category include basic cotton gauze. Also within this category are products from Johnson & Johnson's Ethicon division that sells its Surgicel™ regenerated cellulose product line in various forms. There are other cellulosic type products in the marketplace. The second category of products seeks to enhance coagulation by adding features that can increase clotting enzymatic activity. Such products may include such components as thrombin, fibrinogen, propyl gallate, aluminum sulfate, fully acetylated glucosamine and ϵ-aminocaproic acid. Other hemostatic agents have difficulty adhering to wet tissue and lack a framework onto which a clot can adhere.

Each of these prior art products are deficient in at least one aspect. Products that function solely through absorption of water from the blood tend not to be particularly selective in concentrating the blood constituents useful in clotting such as platelets, erythrocytes and plasmas and therefore are not as effective as other products in enhancing coagulation. The second category of products enhance coagulation by adding components such as thrombin, fibrinogen, propyl gallate, aluminum sulfate, fully acetylated glucosamine and ϵ-aminocaproic acid that increase clotting enzymatic activity. While these products can be very effective at stopping bleeding they can also be quite expensive, have shelf life limitations and in some cases where the components are derived from animals or humans may offer a mechanism for pathogen transfer or allergic reaction. In the third product category, the HemCon™ product suffers from potential allergic side effects, short shelf life and high cost. Some of Z-Medica's QuikClot™ products suffer from problems with high heat of adsorption that can cause significant discomfort to users and limits its utility in heat sensitive parts of the body. One of the QuikClot products is not optimal since it is literally poured onto the wound and must then be carefully washed from the injury. In addition, it has been found that some formulations of prior art products contain one or more ingredients that have a potentially adverse effect upon the product's overall hemostatic ability and when tested individually may in fact encourage bleeding.

A hemostatic material that is biocompatible, provides superior hemostasis, and that can be fabricated into a variety of forms suitable for use in controlling bleeding from a variety of wounds is still sought. This type of hemostatic material is sought for both surgical applications as well as in field treatment of traumatic injuries. In vascular surgery, due to the involvement of the blood vessels, bleeding is particularly problematic. In cardiac surgery, the multiple vascular anastomoses and cannulation sites, complicated by coagulopathy induced by extracorporeal bypass, can result in bleeding that can only be controlled by topical hemostats. Rapid and effective hemostasis during spinal surgery, where control of osseous, epidural, and/or subdural bleeding or bleeding from the spinal cord is not amenable to sutures or cautery, can minimize the potential for injury to nerve roots and reduce the procedure time. In liver surgery, for example, live donor liver transplant procedures or removal of cancerous tumors, there is a substantial risk of continued bleeding. An effective hemostatic material can significantly enhance patient outcome in such procedures. Even in those situations where bleeding is not massive, an effective hemostatic material can be desirable, for example, in dental procedures such as tooth extractions and other oral surgery, as well as the treatment of abrasions, burns, and the like.

There remains a need for an effective hemostatic product that can be delivered in an easy to use form. Until recently, porous carriers or porous articles, e.g. non-woven fibrous articles containing molecular sieves and hydrophilic oxides had not been disclosed for use as hemostatic devices. Such hemostatic articles comprising molecular sieves have now been found to provide ease of application, effective hemostasis, and reduction in exposure of the patient to high temperature increases owing to high heats of adsorption. These products are also useful in surgical applications that were not available using a powdered molecular sieve or hydrophilic oxide product. There is a further need on some occasions for a hemostatic product that is effective for a period of time but that is able to dissolve or disintegrate in the body after the hemostatic effect is no longer needed.

SUMMARY OF THE INVENTION

This invention involves the use of a layer as thin as a few atomic layers to as thick as hundreds of nanometers of silica, a silicate or another effective oxide on a variety of surfaces/materials to accelerate blood coagulation. Other effective oxides include aluminosilicate, $GeO_2$, silicogermanates, $AlPO_4$, metal or main group element aluminophosphates such as silicoaluminophosphates, and $Fe_2O_3$. More than one of these oxides may be used. These ultra-thin layers provide advantages or functionality beyond those that are provided by prior art materials. These advantages include biological inertness after a short time due to the degradation of the ultra-thin oxide layer in vivo, revealing a biologically inert or resorbable surface underneath. An example is nano-$SiO_2$ coated $TiO_2$ particles, which themselves are active in coagulation, but become inert as the thin $SiO_2$ layer leaches off over time.

The silica/silicate layer could also be removed using a biocompatible $SiO_2$ etchant such as amino acid serine/serine-containing peptides/aminoacid oligomers once the layer has done its job. This would leave inert $TiO_2$ behind. Alternatively the nano-$SiO_2$ can be deposited on a polymeric surface which either resorbs into the body or otherwise assumes an inert or beneficial role in the body after the $SiO_2$ layer is gone.

Nano-thin $SiO_2$ coatings can be deposited on a number of surfaces such as powders, substrate surfaces, fibers, non-woven fabrics, polymers, granules or devices via a variety of processes such as sol-gel processes, vapor deposition, or spray processes. Vapor deposition processes that can be used include chemical vapor deposition, atomic layer deposition, plasma-enhanced chemical vapor deposition and electrophoretic deposition. The devices then are sterilized and packaged by appropriate methods.

When the porous carrier is a sheet (and adsorbent) which includes a fibrillated, high surface area fiber and a material that markedly accelerates the contact hemostasis mechanism, the result can be more effective enhancement of coagulation beyond that observed in other products. The nano-coated porous sheet that conforms to irregular surfaces can also be readily used in difficult to access wounds and injuries. Other features desirable in a wound dressing such as biocidal activity can be incorporated either directly into the sheet or into a dressing that includes such a sheet.

DETAILED DESCRIPTION OF THE INVENTION

Hemostasis is the arresting of bleeding, whether by normal vasoconstriction, by an abnormal obstruction, by coagulation or surgical means. Hemostasis by coagulation (which is the subject of the products of the present invention) is dependent upon a complex interaction of plasma coagulation and fibrinolytic proteins, platelets, and the blood vasculature. The present invention provides compositions and materials that physically interact with the hemostatic system to treat or prevent bleeding. In particular, the compositions and materials of preferred embodiments result in coagulation of blood.

Effective delivery of hemostatic agents to wounds is particularly desirable in the treatment of injuries characterized by arterial or venous bleeding, as well as in surgical procedures where the control of bleeding can become problematic, e.g., large surface areas, heavy arterial or venous bleeding, oozing wounds, and in organ laceration or resectioning. The compositions and materials of preferred embodiments can possess a number of advantages in delivery of hemostatic agents to wounds, including but not limited to, ease of application and removal, bioadsorption potential, suturability, antigenicity, and tissue reactivity.

Depending upon the nature of the wound and the treatment method employed, the devices of the present invention can employ different forms that can be made through wet laid processing. For example, a puff, ball, fleece, or sponge-shaped form can be preferable for controlling the active bleeding from artery or vein, or for internal bleeding during laparoscopic procedures. In neurosurgery, where oozing brain wounds are commonly encountered, a sheet form of the hemostatic article can be preferred. Likewise, in oncological surgery, especially of the liver, it can be preferred to employ a sheet form or sponge form of the hemostatic article, which is placed in or on the tumor bed to control oozing. In dermatological applications, a sheet form can be preferred. In closing punctures in a blood vessel, a puff form is generally preferred. Despite differences in delivery and handling characteristic of the different forms, the devices are effective in deploying hemostatic agents to an affected site and to rapidly initiate hemostatic plug formation through platelet adhesion, platelet activation, and blood coagulation. This invention involves the use of a layer as thin as a few atomic layers to as thick as hundreds of nanometers of silica, a silicate or another effective oxide on a variety of surfaces/materials to accelerate blood coagulation. Other effective oxides include $GeO_2$, silicogermanates, $AlPO_4$, silicoaluminophosphates, and $Fe_2O_3$. More than one of these oxides may be used. These ultra-thin layers provide advantages or functionality beyond those that are provided by prior art materials. These advantages include biological inertness after a short time due to the degradation of the ultra-thin oxide layer in vivo, revealing a biologically inert or resorbable surface underneath. An example is $SiO_2$ coated $TiO_2$ particles, which themselves are active in coagulation, but become inert as the nano $SiO_2$ layer leaches off over time. The silica/silicate layer could also be removed using a biocompatible $SiO_2$ etchant such as amino acid serine/serine-containing peptides/amino acid oligomers once the layer has done its job. This would leave inert $TiO_2$ behind. Alternatively the $SiO_2$ can be deposited on a polymeric surface which either resorbs into the body or otherwise assumes an inert or beneficial role in the body after the $SiO_2$ layer is gone. Nano $SiO_2$ coatings can be deposited on a number of surfaces such as powders, substrate surfaces, fibers, non-woven fabrics, polymers, granules or devices via a variety of processes such as sol-gel processes, vapor deposition, or spray processes. Vapor deposition processes that can be used include chemical vapor deposition, atomic layer deposition, plasma-enhanced chemical vapor deposition and electrophoretic deposition. The devices then are sterilized and packaged by appropriate methods.

The nanocoating may have a thickness from about 5 to 750 nm thick, preferably from about 10 to 500 nm thick and more preferably from about 10 to 250 nm thick. The resulting coating, expressed in wt-% of the nanocoated article, may be controlled to a significant extent. Oxide nanocoating content varies with the thickness of deposited film and the uniformity of the thickness. In the case of a $SiO_2$ nanocoating, if the nanocoated articles have a surface area of 10 $m^2/g$ then for a thickness range of 5 to 100 nm $SiO_2$, assuming a $SiO_2$ density of 2 g/cc and a uniform nanocoating thickness, the $SiO_2$ content of the nanocoated article is 10 wt-% to 200 wt-%, respectively. A 5 nm coating on a 1 $m^2/g$ surface area substrate results in 1 wt-% $SiO_2$ and a 100 nm coating on a 1 $m^2/g$ substrate gives a $SiO_2$ content of 20 wt-% $SiO_2$.

The materials which can be used as the porous carriers for the adsorbent are any article which can support an effective amount of the oxide coated-sheet composite and can be applied to the particular wound being treated. The porous carrier can be composed of natural or synthetic materials and can be woven or non-woven fibrous articles. Oxide-nano-coated non-woven articles can be prepared by textile-, paper-, extrusion type and a combination or hybrid of processes. The product can be prepared using a variety of fibers including cellulose, aramid, acrylic, polyester, polyolefin, including fibrillated polyethylene and polypropylene, Spectra™ polyethylene (a Honeywell product), chemically modified cellulose fibers such as lyocell and rayon, and synthetic polymers such as Zylon™ (Zylon is also called PBO after its chemical structure, poly(p-phenylene-2,6-benzobisoxazole) and Vectran® (a liquid crystal polymer (LCP)) Various binders can also be used in preparing the sheets, some of which may have functional groups that can aid in the release of coagulation enhancing agents.

Preferably, the fibers employed in the present invention are fibrillated to increase the surface area and the capacity to retain higher loadings of nanocoatings and other additives.

Suitable fibril-forming thermoplastic polymers may include polymers and copolymers from vinyl chloride, vinyl acetate, acrylonitrile, styrene, butadiene, vinylidene chloride, ethylene and propylene, and condensation polymers, for example polyamide and polyesters, e.g. of glycols and aromatic dicarboxylic acids. Blends of fiber-forming thermoplastic polymer materials may also be used. Natural fibers or fibers chemically derived from natural fibers such as cellulose, rayon and lyocell may also be fibrillated.

A single hemostatic substrate or combination of hemostatic substrate comprising the porous carrier of the present invention can be employed. Different substrate forms can be preferred, for example, puff, fleece, fabric or sheet. In this specification, the term "fleece" is used as a broad term in accordance with its ordinary meaning and includes any fibrous material treated to be flexible, malleable or the like. A fleece may be provided in a non-woven form or in a sheet form. It is to be understood that the fibrous fleece can be treated or coated in any suitable manner to enhance its hemostatic properties. The term "puff" is also used as a broad term in accordance with its ordinary meaning and includes any fibrous material arranged into a soft ball or pad. A puff may be constructed using a sheet. The term "sponge" is also used as a broad term in accordance with its ordinary meaning and includes a material configured to absorb fluids such as blood. A sponge may be constructed using, without limitation, a fleece, puff, fiber, sheet or the like alone or in combination with another material. A homogeneous mixture of different substrate-forming materials can be employed, or composite substrates can be prepared from two or more different formed substrates. In certain embodiments, it can be desirable to add an auxiliary hemostatic agent to the adsorbent hemostatic agents of the present invention. Any suitable hemostatic agent can be deposited upon the substrates of preferred embodiments. Among the hemostatic agents that can be used are bioabsorbable microporous polysaccharide microspheres, clotting factor concentrates, recombinant Factor VIIa (NOVOSEVEN®); alphanate FVIII concentrate; bioclate FVIII concentrate; monoclate-P FVIII concentrate; haemate P FVIII; von Willebrand factor concentrate; helixate FVIII concentrate; hemophil-M FVIII concentrate; humate-P FVIII concentrate; hyate-C®. Porcine FVIII concentrate; koate HP FVIII concentrate; kogenate FVIII concentrate; recombinate FVIII concentrate; mononine FIX concentrate; and fibrogammin P FXIII concentrate. Such hemostatic agents can be applied to the substrate in any suitable form (powder, liquid, in pure form, in a suitable excipient, on a suitable support, or the like).

A single hemostatic agent or combination of hemostatic agents can be employed. Preferred loading levels for the hemostatic agent on the substrate can vary, depending upon the nature of the substrate and hemostatic agent, the form of the substrate, and the nature of the wound to be treated.

Hemostatic fabrics can also be prepared from sheets. It is generally preferred that one side of the fabric has a smooth surface and the other side of the fabric has a rough surface. However, in certain embodiments, a fabric having two rough sides can be preferred, such as, for example, for use in connection with an irregular wound, or a deep wound, such as a potentially lethal groin injury. In preferred embodiments, the rough surface is exposed to the wound so as to maximize contact of the fibers with the wound, resulting in an improved hemostatic effect and superior adherence to the wound as well as contact of the nano-oxide coatings with the blood flowing from the wound.

The hemostatic fabric can be provided in the form of a sheet of a pre-selected size. Alternatively, a larger sheet of hemostatic fabric can be cut, trimmed, or folded to provide a size and shape appropriate to the wound. Alternatively, trimmed sheets can be stacked into multilayers or laminates. Although the hemostatic fabric is biocompatible in cutaneous or topical applications, it can be removed from the wound after a satisfactory degree of hemostasis is achieved, or it can be left in place until the wound is healed. Hemostatic fabric can be useful as artificial skin, and/or can provide antibiotic properties. A hemostatic sponge can be prepared according to methods known in the art for preparing a porous sponge from a biocompatible or bioabsorbable polymeric material. Such methods typically involve preparation of a solution of the polymeric material, crosslinking agents, and foaming agents. The sponge can be coated with a hemostatic nanocoating of oxide during formation of the sponge.

While it is generally preferred to apply the hemostatic material directly to the wound, and while the hemostatic material exhibits satisfactory adhesion to many types of wounds, in certain embodiments it can be preferred to incorporate the hemostatic material into a wound dressing including other components such as porous wovens, nonwovens or films.

To ensure that the hemostatic material remains affixed to the wound, a suitable adhesive can be employed, for example, along the edges of one side of the hemostatic structure. Although any adhesive suitable for forming a bond with skin can be used, it is generally preferred to use a pressure sensitive adhesive. Pressure sensitive adhesives are generally defined as adhesives that adhere to a substrate when a light pressure is applied but leave no residue when removed. Pressure sensitive adhesives include, but are not limited to, solvent in solution adhesives, hot melt adhesives, aqueous emulsion adhesives, calenderable adhesive, and radiation curable adhesives. Solution adhesives are preferred for most uses because of their ease of application and versatility. Hot melt adhesives are typically based on resin-tackified block copolymers. Aqueous emulsion adhesives include those prepared using acrylic copolymers, butadiene styrene copolymers, and natural rubber latex. Radiation curable adhesives typically consist of acrylic oligomers and monomers, which cure to form a pressure sensitive adhesive upon exposure to ultraviolet lights.

The most commonly used elastomers in pressure sensitive adhesives include natural rubbers, styrene-butadiene latexes, polyisobutylene, butyl rubbers, acrylics, and silicones. In preferred embodiments, acrylic polymer or silicone based pressure sensitive adhesives are used. Acrylic polymers generally have a low level of allergenicity, are cleanly removable from skin, possess a low odor, and exhibit low rates of mechanical and chemical irritation. Medical grade silicone pressure sensitive adhesives are preferred for their biocompatibility.

Among the factors that influence the suitability for a pressure sensitive adhesive for use in wound dressings of preferred embodiments is the absence of skin irritating components, sufficient cohesive strength such that the adhesive can be cleanly removed from the skin, ability to accommodate skin movement without excessive mechanical skin irritation, and good resistance to body fluids. In preferred embodiments, the pressure sensitive adhesive comprises a butyl acrylate. While butyl acrylate pressure sensitive adhesives are generally preferred for many applications, any pressure sensitive adhesive suitable for bonding skin can be used. Such pressure sensitive adhesives are well known in the art.

As discussed above, the hemostatic materials of preferred embodiments generally exhibit good adherence to wounds such that an adhesive, for example, a pressure sensitive adhesive, is not necessary. However, for ease of use and to ensure that the hemostatic material remains in a fixed position after application to the wound, it can be preferable to employ a pressure sensitive adhesive.

While the hemostatic fabrics and other hemostatic materials of preferred embodiments generally exhibit good mechanical strength and wound protection, in certain embodiments it can be preferred to employ a backing or other material on one side of the hemostatic material. For example, a composite including two or more layers can be prepared, wherein one of the layers is the hemostatic material and another layer is, e.g., an elastomeric layer, gauze, vapor-permeable film, waterproof film, a woven or nonwoven fabric, a mesh, or the like. The layers can then be bonded using any suitable method, e.g., adhesives such as pressure sensitive adhesives, hot melt adhesives, curable adhesives, and application of heat or pressure such as in lamination, physical attachment through the use of stitching, studs, other fasteners, or the like.

Advantage can be taken of the surface charge characteristics of the fibers and fillers by ion exchanging or otherwise loading additional functional ions such as $Ca^{2+}$ to aid coagulation. Addition of anionic polyelectrolytes may also add ion exchange capacity. The fiber composition and its degree of fibrillation can also be varied to enhance and optimize coagulation.

It is believed that the hemostatic devices of the invention do not require an additional hemostatic agent to function effectively to control bleeding, e.g., hemorrhage of a parenchymal organ. As a result, the hemostatic devices of the invention which do not further contain a hemostatic agent have good thermal stability and can be stored for months to a few years without refrigeration and loss of effectiveness. Such embodiments of the invention are useful for various medical situations and are particularly useful for field and emergency use, since each may be stored in a ready-to-use state for a lengthy period, even in the absence of refrigeration. Such devices of the invention also are less expensive to make and/or use compared to hemostatic devices which contain a further hemostatic agent to achieve a comparable level of hemostatic activity. In certain embodiments, the hemostatic devices of the invention further include a therapeutically effective amount of one or more therapeutic agents, such as an agent which promotes wound-healing. Agents which promote wound-healing include anti-inflammatory agents such as agents which inhibit leukocyte migration into the area of surgical injury, anti-histamines; agents which inhibit free radical formation; and bacteriostatic or bacteriocidal agents. In general, a therapeutically effective amount means that amount necessary to delay the onset of, inhibit the progression of, or halt altogether the particular condition being treated. Generally, a therapeutically effective amount will vary with the subject's age, condition, and sex, as well as the nature and extent of the condition in the subject, all of which can be determined by one of ordinary skill in the art. The dosage of therapeutic agent contained in the hemostatic devices of the invention may be adjusted to accommodate the particular subject and condition being treated. As used herein, the phrase, "agents which promote wound-healing" refers to agents, the administration of which, promote the natural healing process of a wound. Agents that promote wound-healing include anti-inflammatory agents, agents which inhibit free radical formation, and bacteriostatic or bacteriocidal agents.

Anti-inflammatory agents are agents that inhibit or prevent an immune response in vivo and include: (i) agents which inhibit leukocyte migration into the area of surgical injury ("leukocyte migration preventing agents"), and anti-histamines. Representative leukocyte migration preventing agents include silver sulfadiazine, acetylsalicylic acid, indomethacin, and Nafazatrom. Representative anti-histamines include pyrilamine, chlorpheniramine, tetrahydrozoline, antazoline, and other anti-inflammatories such as cortisone, hydrocortisone, beta-methasone, dexamethasone, fluocortolone, prednisolone, triamcinolone, indomethacin, sulindac, its salts and its corresponding sulfide, and the like.

Representative agents which inhibit free radical formation include antioxidants that inhibit the formation and/or action of oxide products, superoxide dismutase (SOD), catalase, glutathione peroxidase, b-carotene, ascorbic acid, transferrin, ferritin, ceruloplasmin, and desferrioxamine α-tocophenol.

Representative bacteriostatic or bacteriocidal agents include antibacterial substances such as β-lactam antibiotics, such as cefoxitin, n-formamidoyl thienamycin and other thienamycin derivatives, tetracyclines, chloramphenicol, neomycin, gramicidin, bacitracin, sulfonamides; aminoglycoside antibiotics such as gentamycin, kanamycin, amikacin, sisomicin and tobramycin; nalidixic acids and analogs such as norfloxican and the antimicrobial combination of fluoroalanine/pentizidone; nitrofurazones, and the like.

The hemostatic devices of the invention can contain one or more therapeutic agents, alone or in combination with one or more hemostatic agents.

Various additives, optionally, can be incorporated into the hemostatic devices of the invention without substantially reducing the hemostatic activity of these devices. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled within the woven sheets of the present invention, and with each other, in a manner such that there is no interaction which would substantially impair the desired hemostatic activity.

What is claimed is:
1. A hemostatic article consisting of:
    a) a fibrous substrate consisting of one or more fibers, said fibers being selected from the group consisting of lyocell fibers, rayon fibers, aramid fibers, acrylic fibers, polyester fibers, polyolefin fibers, poly(p-phenylene-2,6-benzobisoxazole) fibers, liquid crystal polymer fibers and combinations thereof; and
    b) a uniform film coating having a thickness of 5 nm to 100 nm on a surface of the fibrous substrate,
    said 5 nm to 100 nm uniform film coating consisting of a hemostatically effective, hydrophilic oxide, wherein the hemostatically effective, hydrophilic oxide coating consists of $SiO_2$, a silicate, aluminosilicate, $GeO_2$, silicogermanate, germanate, $AlPO_4$, a metal or main group element aluminophosphate, $Fe_2O_3$, or a mixture thereof, and
    wherein the uniform film coating on the fibrous substrate is formed by chemical vapor deposition, plasma-enhanced chemical vapor deposition or atomic layer deposition.

2. The hemostatic article of claim 1 wherein the substrate consists of a non-woven fibrous substrate.

3. The hemostatic article of claim 1 wherein the substrate consists of a woven fibrous substrate.

4. The hemostatic article of claim 1 wherein the hemostatically effective, hydrophilic oxide consists of an aluminosilicate.

5. The hemostatic article of claim 1 wherein said uniform film coating consists of a mixture of silica and aluminosilicate.

6. The hemostatic article of claim 1 wherein the hemostatically effective, hydrophilic oxide consists of $SiO_2$.

* * * * *